(12) United States Patent
Schrier et al.

(10) Patent No.: US 6,850,633 B2
(45) Date of Patent: Feb. 1, 2005

(54) DEVICES AND METHODS FOR READING AND INTERPRETING GUAIAC-BASED OCCULT BLOOD TESTS

(75) Inventors: Wayne H. Schrier, Half Moon Bay, CA (US); John Warwick Silzel, Yorba Linda, CA (US); Richard Sergei Matusewicz, San Jose, CA (US); Ronald Joseph Schoengold, Saratoga, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 609 days.

(21) Appl. No.: 09/792,461

(22) Filed: Feb. 23, 2001

(65) Prior Publication Data

US 2002/0136436 A1 Sep. 26, 2002

(51) Int. Cl.⁷ .......................... G06K 9/00; G01N 33/72; G01N 21/00
(52) U.S. Cl. ...................... 382/128; 382/133; 382/134; 436/66; 436/164
(58) Field of Search ................................ 382/128, 133, 382/134; 436/66, 164

(56) References Cited

U.S. PATENT DOCUMENTS

| | | | |
|---|---|---|---|
| 2,838,377 A | 6/1958 | Fonner | 23/230 |
| 3,012,976 A | 12/1961 | Adams, Jr. et al. | 252/408 |
| 3,092,463 A | 6/1963 | Adams, Jr. et al. | 23/253 |
| 3,252,762 A | 5/1966 | Adams, Jr. et al. | 23/253 |
| 3,290,117 A | 12/1966 | Adams, Jr. et al. | 23/253 |
| 3,918,910 A | 11/1975 | Soya et al. | 23/253 R |
| 3,996,006 A | 12/1976 | Pagano | 23/253 |
| 4,329,317 A | 5/1982 | Detweiler et al. | 422/58 |
| 4,365,970 A | 12/1982 | Lawrence et al. | 436/66 |
| 4,382,064 A | 5/1983 | Detweiler et al. | 422/58 |
| 4,486,536 A | 12/1984 | Baker et al. | 436/66 |
| 4,521,520 A | 6/1985 | Jacke | 436/66 |
| 4,645,743 A | 2/1987 | Baker et al. | 436/66 |
| 4,678,757 A | 7/1987 | Rapkin et al. | 436/169 |
| 4,789,629 A | 12/1988 | Baker et al. | 435/7 |
| 5,100,619 A | 3/1992 | Baker et al. | 422/58 |
| 5,106,582 A | 4/1992 | Baker | 422/58 |
| 5,150,971 A | 9/1992 | Strong et al. | 383/84 |
| 5,264,181 A | 11/1993 | Schreiber | 422/58 |
| 5,304,468 A | 4/1994 | Phillips et al. | 435/14 |
| 5,310,680 A | 5/1994 | Baker et al. | 436/66 |
| 5,316,732 A | 5/1994 | Golukhov et al. | 422/102 |
| 5,337,426 A | 8/1994 | Matusewicz et al. | 4/661 |
| 5,391,498 A | 2/1995 | Baker et al. | 436/66 |
| 5,408,535 A | 4/1995 | Howard, III et al. | 382/1 |
| 5,412,819 A | 5/1995 | Matusewicz et al. | 4/661 |
| 5,432,865 A * | 7/1995 | Kasdan et al. | 382/128 |
| 5,449,622 A | 9/1995 | Yabe et al. | 436/63 |
| 5,449,898 A | 9/1995 | Dosmann | 250/208.1 |
| 5,701,181 A | 12/1997 | Boiarski et al. | 356/446 |
| 5,790,761 A | 8/1998 | Heseltine et al. | 395/22 |
| 5,846,490 A | 12/1998 | Yokota et al. | 422/66 |
| 6,235,532 B1 * | 5/2001 | Uttamchandani et al. | 436/60 |
| 6,418,236 B1 * | 7/2002 | Ellis et al. | 382/128 |
| 6,563,575 B1 * | 5/2003 | Nichols et al. | 356/237.1 |

* cited by examiner

*Primary Examiner*—Daniel Miriam
*Assistant Examiner*—Shefali Patel
(74) *Attorney, Agent, or Firm*—William H. May; D. David Hill; Hogan & Hartson, LLP

(57) ABSTRACT

A medical analysis system for reading and interpreting an occult blood test (OBT) device is provided. The instant system comprises an image sensor for capturing an image of the entire test area of the fecal occult blood test (FOBT) device and for converting the image into a digital data. The system further comprises a data processor conventionally coupled to the image sensor. The data processor compares the digital data with pre-determined threshold conditions of a positive FOBT by utilizing a spectrographic and morphologic image analysis algorithm and determines a presence of the occult blood in the sample. A hue angle analysis for data processing may be used. A method of performing FOBT on a sample is also provided.

27 Claims, 4 Drawing Sheets

DEVICES AND METHODS FOR READING AND INTERPRETING GUAIAC-BASED OCCULT BLOOD TESTS

BACKGROUND OF THE INVENTION

1. Area of the Art

The present invention relates to determining the presence of occult blood in fecal matter, and more particularly to a system for reading and interpreting guaiac-based occult blood tests.

2. Description of the Prior Art

Each year, more than 130,000 Americans are diagnosed with colorectal cancer. Of those afflicted, an estimated 56,000 die—a death toll that ranks this cancer as the second highest, for women and men, among all types of cancers. Scientific evidence suggests that the majority of colon cancers arise from the evolution of normal mucosa progressing into adenomas and finally to adenocarcinomas. Adenoma removal correlates with a reduced risk of rectal carcinomas; analogously, the removal of adenomatous polyps, reduces the likelihood of colon cancer (U.S. Pat. No. 5,790,761). Unlike other forms of cancer, early diagnosis and treatment of colorectal cancer results in a high cure rate of more than 90%. If, however, the disease is not detected until the later stages, the cure rate drops drastically to 25% or less (U.S. Pat. No. 5,264,181). Thus, early detection of the disease is critical to successful treatment of colorectal cancer.

Occult (hidden) blood in feces is an early sign of colorectal cancer, adenomas and polyps. It is undetectable to the naked eye, because the blood is present in minute amounts. Tests and procedures for detecting occult blood in fecal matter are well-known. One of the most successful tests is offered by Beckman Coulter, Inc. (Fullerton, Calif.) under the trademark HEMOCCULT® and disclosed in U.S. Pat. No. 3,996,006 issued to J. F. Pagano. Briefly, a thin smear of fecal matter is applied to one side of the guaiac paper. Then, a developing solution, such as hydrogen peroxide, is applied to the opposite side of the guaiac paper. If blood is present in the fecal matter, the guaiac reaction will color the paper blue. Recently, a similar but more sensitive test has been introduced under trademark HEMOCCULT® SENSA® by Beckman Coulter, Inc.

Guaiac-based tests are rapid, simple, disposable, and convenient for use in doctors' offices, hospitals and other point-of-care locations for the quick diagnosis of conditions associated with colorectal cancer. However, since these tests are visually-read and the results are recorded manually, the conventional guaiac test formats are not suitable for use in high volume settings required by many diagnostic laboratories.

Another problem associated with these guaiac tests is instability of the test results. Test paper must be examined within 60 seconds after the addition of the developer to prevent inaccurate interpretation of the test results due to color fading. Additionally, some conventional guaiac tests suffer from insufficient sensitivity, which leads to a relatively high number of negative test results in fecal samples from known bleeding patients.

Finally, in certain applications, semiquantitative data may have greater value than qualitative results. Conventional visual reading methods of guaiac test interpretation, however, provide only qualitative results.

In view of the deficiencies of the related art, there is a need for an accurate and highly sensitive device for automated or semi-automated interpretation of fecal occult blood tests (FOBTs). There is also a need for novel, highly sensitive, and semiquantitative analysis methods for use in occult blood testing.

SUMMARY OF THE INVENTION

Accordingly, it is an object of the present invention to provide an automatic or semi-automatic device, which captures the FOBT results and stores them in an electronic file. The electronic file may be conveniently retrieved by a healthcare professional at any time after the test, for qualitative and semiquantitative data interpretation and manipulation. It is also an object of the present invention to provide a method for accurate reading and interpreting of FOBT devices.

In recent years, a variety of optical devices have been successfully used for reading and interpreting of test articles impregnated with liquid biological samples, such as blood, serum, saliva, and urine (U.S. Pat. No. 3,918,910 ("the '910 patent"); U.S. Pat. No. 5,304,468 ("the '468 patent"); U.S. Pat. No. 5,449,622 ("the '622 patent"); U.S. Pat. No. 5,449,898 ("the '898 patent"); U.S. Pat. No. 5,701,181 ("the '181 patent"); U.S. Pat. No. 5,846,490 ("the '490 patent"); and U.S. Pat. No. 5,408,535 ("the '535 patent"). However, screening for colorectal cancer typically requires the analysis of fecal samples and a different test format.

In the conventional testing of liquid samples, the test articles are saturated with all reagents required for an analyte identification. The addition of the analyte contained in the liquid sample to the test article leads to the development of a signal, which is detected by a sensor. In FOBTs, on the other hand, the sample itself does not produce a detectable signal until a developer reagent is added to the test device. Also, conventional methods require localization of the optical signal to a discrete area of the testing device. In fecal sample analysis, however, the optical signal is not localized. Instead, color patches may develop substantially anywhere on or around the sample. Therefore, measuring optical signals in discrete areas of a test device would likely miss the developed color elsewhere on the slide. In FOBTs, the entire testing area of the testing device has to be evaluated to locate areas containing the reacted guaiac color and to determine if the color patches are regarded as true positive test results. Therefore, none of the conventional devices of the liquid sample analysis can accommodate the processing and interpretation of FOBTs.

The instant medical analysis system for reading and interpreting FOBT devices overcomes the deficiencies of the related art. FOBT devices have a continuous test area matrix for spreading a fecal sample and adding a developer. The test area reacts with the sample, which may be in a liquid, solid or semi-solid form, and the developer. If blood is present in the sample color patches are formed on or around the sample. The instant system comprises an image sensor for capturing an image of the entire test area of the FOBT device and for converting the image into a digital data. The system further comprises a data processor conventionally coupled to the image sensor. The data processor compares the digital data with predetermined threshold conditions of a positive FOBT by utilizing a spectrographic and morphologic image analysis algorithm and determines the presence of the occult blood in the sample.

Examples of acceptable image sensors include, but are not limited to, charge-coupled devices (CCD), charge injection devices, translational stage and optical scanners, color complementary metallic oxide semiconductors, photovoltaic diode arrays, color video cameras with frame-grabbing software, and photographic film. The image sensors of the present invention may also include additional electronic and optical components necessary for capturing the image and converting it into the digital data.

The data processor may comprise a computer system. In one embodiment, the computer system utilizes a hue angle image analysis to identify positive test patch(es) and to determine a presence of the occult blood in the sample. In another embodiment, the computer system also determines a relative mass of the blood present in the sample by correlating the mass with a size of the identified positive test patch. When a plurality of the positive patches are identified, the relative mass of the blood present in the sample is correlated to a cumulative size of the positive test patches. Typically, the system of the present invention also includes an illumination source for illuminating the test area of the FOBT device with a light and a sample positioner for positioning and holding the FOBT device.

In another aspect, the present invention provides a medical analysis system utilizing a hue angle analysis algorithm for reading and interpreting a FOBT device. The system comprises an illumination source for illuminating the test area of the FOBT device with light. The system further comprises an image sensor for detecting the light reflected from the test area. The image sensor generates an image of the entire test area and converts the image into digital data. The system further comprises a data processor coupled to the image sensor. The data processor applies a hue angle analysis to the received digital data, compares the digital data with predetermined threshold conditions of a positive POBT, and identifies at least one positive test patch indicative of the presence of the occult blood in the sample.

In still another aspect, the present invention provides a method of performing an FOBT on a fecal sample. The method comprises the steps of:

(a) placing the sample on a test area of the FOBT device;

(b) applying a developer to the test area to produce color patches on or around the sample;

(c) capturing an image of the test area with an image sensor and converting the image into digital data; and (d) comparing the digital data with predetermined threshold conditions of a positive FOBT by utilizing a data processor with a spectrographic and morphologic image analysis capability;

(e) comparing the size of each color patch with a preselected threshold value to identify a positive test patch; and (f) correlating a presence of at least one positive test patch on the test device with a presence of the occult blood in the sample.

The systems and methods of the present invention meet the needs set forth and provide a number of advantages. This invention significantly improves reproducibility of the test results by eliminating variations associated with a variability in human visual acuity. High reproducibility of the testing results is achieved in the present invention by selecting objective clinical thresholds for positive test identification.

The related art utilizes a single optical parameter, such as reflectance (the '181, '469, and '535 patents), turbidity, or absorption (the '622 patent) to detect presence of an analyte. Consequently, the conventional methods are very sensitive to uniformity of illumination (brightness, color saturation) and image resolution. Unlike the prior art, the present system utilizes spectrographic and morphologic image analysis, which is substantially independent of the above factors. Therefore, the system of the present invention provides improved accuracy of FOBT interpretation and test replication.

The system of the present invention may be easily adapted to provide additional convenient, user-friendly features. For example, the system of the present invention may automatically read and enter into the image-containing electronic file relevant markings. The markings may include bar codes, lot numbers, patient information and test type, image alignment marks, and other useful information. These markings may be factory-printed, affixed by the caregiver(s), or handwritten on the test device.

The present invention can also utilize positive and negative control indicators of the FOBT devices to verify their proper operation. Additionally, the system may provide the verification of the correct placement and a suitable quantity of stool sample and developer to the test area of the FOBT device. After identification of positive test patches, their dimensions may be measured to provide a semiquantitative measurement of blood present in the sample. Remote data analysis, offline post analysis, and/or re-analysis of archived images, and remote or on-site archiving of the test image results are additional benefits of the systems and methods of the present invention. Thus, the present invention provides accurate, efficient, and convenient systems and methods for reading and interpretation of FOBT devices.

The present invention may be particularly beneficial when used in conjunction with popular point-of-care or near-patient FOBT devices such as HEMOCCULT® and HEMOCCULT® SENSA® (Beckman Coulter, Inc., CA). For example, semiquantitative analysis of the devices provided by the present invention may supply a valuable diagnostic information to medical practitioners, which is not available in visual interpretation of the tests.

DESCRIPTION OF THE FIGURES

The above-mentioned and other features of this invention and the manner of obtaining them will become more apparent, and will be best understood by reference to the following description, taken in conjunction with the accompanying drawings. These drawings depict only typical embodiments of the invention and do not therefore limit its scope.

FIG. 2A shows a raw 8-bit Red/Green/Blue (RGB) image, before processing;

FIG. 2B shows a black-and-white, 8-bit gray scale image obtained by hue angle data analysis of the raw image shown in FIG. 2A;

FIG. 2C shows a digital "binary" image obtained from the 8-bit gray scale image shown in FIG. 2B. Black color (value "0") is assigned to the areas of the image with computed hue angles below the preset threshold typical of positive FOBTs. White color (value "1") is assigned to the areas of the image with computed hue angles above the preset threshold typical of positive FOBTs.

FIG. 2D shows a smoothed image. A median filter was applied to the binary image shown in FIG. 2C to remove the "speckle" artifacts and to smooth the borders of the white objects.

FIG. 2E shows assigning numbers to each white object of FIG. 2D.

DETAILED DESCRIPTION OF THE INVENTION

Figure 1:
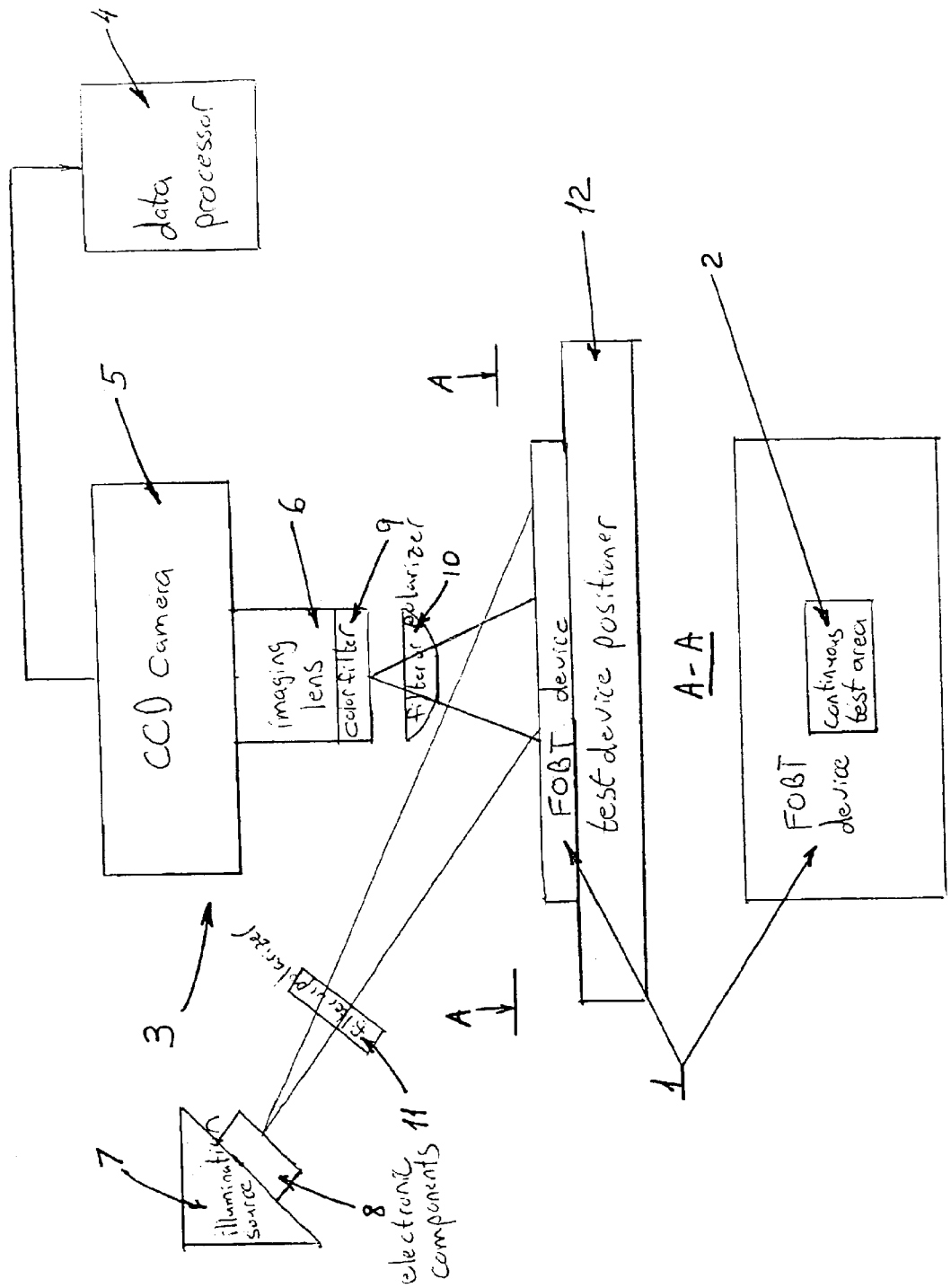
FIG. 1 shows a schematic diagram of a medical analysis system utilizing a color CCD camera as an image sensor in accordance with one embodiment of the present invention.

Referring to FIG. 1, the present invention provides a medical analysis system for reading and interpreting an FOBT device 1. The FOBT device typically has a continuous test area 2 to which a sample and a developer are applied. The sample may be liquid, semi-solid, or solid, but more typically the sample is semi-solid or solid. The test area typically comprises guaiac paper or another guaiac material. The sample is spread on the test area and then the developer is applied. The test area reacts with the sample and the developer and color patches develop on or around the sample. The instant system is used to analyze the developed color patches and to determine whether they constitute a positive test result indicative of the presence of the occult blood in the sample.

The system comprises an image sensor 3 for capturing an image of the entire test area of the FOBT device and for converting the image into digital data. The system further comprises a data processor 4 conventionally coupled to the image sensor 3. The data processor 4 compares the digital data with predetermined threshold conditions of a positive FOBT by utilizing a spectrographic and morphologic image analysis algorithm and determines a presence of the occult blood in the sample.

Examples of acceptable image sensors 3 include, but are not limited to, charge-coupled devices (CCD), charge injection devices, translational stage and optical scanners, color complementary metallic oxide semiconductors, photovoltaic diode arrays, color video cameras with frame-grabbing software, and photographic film. The image sensors of the present invention may also include additional electronic and optical components necessary for capturing the image and converting it into the digital data. Examples of optical components include, but are not limited to, lenses, mechanical or optical scanners, shutters, irises, and filters.

Referring to FIG. 1, the system of the present invention may utilize a color CCD camera 5 with an imaging lens 6 as the image sensor. The small size, electrical efficiency, and cost-effectiveness of CCDs have made them the imaging units of choice in a broad range of applications from consumer video cameras to digital color printers and high-speed scanners. Recently, the use of CCD-based imaging systems for detecting and recording optical signals from labeled analytes in biological samples have been described (U.S. Pat. Nos. 5,552,272; 5,301,671; 5,891,656; and 5,965,410). By utilizing software routines, the CCD camera may be automatically calibrated. The performance of CCD cameras may be further improved by correcting for their unit-to-unit variability in the detector response. CCD cameras afford high throughput advantages over serial scanning techniques, at less cost than confocal optics. In one embodiment of the present invention, a color digital camera, MAVICA® (Sony, Japan), which provides 8-bit RGB files in the standard .TIF format, was used. Alternatively, a digital monochrome camera having a plurality of color filters 9 may be used in the instant system.

Referring to FIG. 1, in a preferred embodiment, the system also comprises an illumination source 7 for illumination of the test area of the FOBT device with a light. The illumination source may be a source of ambient light; diffused, focused, or collimated incident light; or fiberoptically guided light including evanescent wave illumination. Examples of possible illumination sources include, but are not limited to, incandescent lamps, fluorescent lamps, electrochemiluminescent devices, arc discharge lamps, stroboscopic-type flash lamps, light-emitting diodes, fiberoptic illuminators, lasers, and combinations thereof. The system may also include optical or electronic components 8 for directing the light from the illuminating source onto the test area of the FOBT device. Examples of suitable optical components include, but are not limited to, lenses, prisms, mechanical or optical scanners, shutters, irises, filters, fiber optical devices, such as fiber optic bundles, and combinations thereof. In some applications, the system may include a plurality of illumination sources and a plurality of the image sensors. Since the present system utilizes a spectrographic and morphologic image analysis for identification of positive tests, the system does not impose strict requirements on the light uniformity. Instead, variations in illumination are compensated by flat fielding method of image analysis briefly described below.

Referring to FIG. 1, in one embodiment, the test area 2 of an FOBT device 1 is illuminated by a light bulb or another optical or fiberoptical illuminator, such as condensers, diffusers, reflective elements, light pipes, or ring lights. An image of the test area 2 is captured by a color scanning or imaging device, such as a CCD camera 5 with an imaging lens 6 and automatically analyzed by the data processor 4. Optional elements, such as filters and/or polarizers 10 and 11, may be used to modify the spectra of the illumination source 7 and/or reflected light to optimize sensitivity of the system to the desired color development or to minimize the scattered light background.

The system may also include a test device positioner 12 for positioning and holding the FOBT device in a predetermined location. The test positioner may have automation features that automatically shuttle stacks of the test devices through the system. The system may also include a dispensing system for automatic dispensing of developer solutions onto each FOBT device and a device for timing the image development period. Such devices are well-known to those trained in the art, and, therefore, do not need a detailed description.

The data processor 4 may comprise a computer system utilizing a spectrographic and morphologic image analysis algorithm. For the purpose of the present invention, the term "morphologic image" refers to an image of an area of any regular or irregular shape. Such algorithms are used to analyze both the color and the morphology of a test area. Due to the irregularity and non-uniformity of fecal samples that have been applied to the test area, it is necessary to derive algorithms that correlate with clinical findings in patients that are diagnostically useful.

Specific methods and algorithm for spectrographic and/or morphologic image analysis are well-known in the art and will not be discussed here in great detail. (See "Digital Image Processing" by William K. Pratt, $2^{nd}$ Edition, John Wiley & Sons, Inc., New York, 1991.) Examples of such image and morphologic analysis methods include, but are not limited to, a hue angle image analysis; a flat-fielding analysis for reducing a non-uniform illumination effect on the test sample; a vector analysis for better object color discrimination in the image; an image factor analysis coupled with a principal component regression method for providing a multi-wavelength spectroscopic analysis of the image; a mean-centering analysis for reducing any illumination variance on the test sample during formation of the image; and their combinations; object location, counting, and classification, as well as measurement of object areas, perimeters, center of mass coordinates, and the comparison of these or other measured or computed object parameters to expected values or to the location of specific areas, targets, or features printed, developed, or produced on the test device.

In accordance with embodiments of the present invention, image factor analysis may be coupled with principal components regression (2-D PCR) using red/green/blue (RGB), hue/saturation/intensity (HSI), or other color model systems. Generally, the methods commonly used for multiwavelength spectroscopy are applicable to the "3-wavelength" images, if the three color channels for each image pixel are treated as separate wavelength detectors.

Mean-centering of image data or other mathematical methods may be used to remove variance in the image which corresponds to simultaneous change in all three color channels (e.g., primarily a "brightness" change not indicative of coloration). The goal in these processes would be to increase the instrument's immunity to changes in illumination.

Flat-fielding operations involve processing the image data prior to the object location in order to remove or reduce the effects of non-uniform illumination across the viewed area. Many methods of flat fielding are described in the image analysis literature and are well-known to those trained in the art.

A vector analysis for better object discrimination in the image is typically based on a multiplication of the n-vector (e.g., the 3-element vector containing red, green, and blue intensity information in the case of an RGB image) representing a given pixel in the image data by one or more n-vectors which seek to isolate particular color/brightness/saturation values corresponding to the desired image features.

Feature-specific convolutions of image data allows the removal of non-FOBT image features (speckles, dust, background reflections, etc.), while enhancing features likely to be of diagnostic usefulness.

More sophisticated morphological analysis of images, leading to so-called "expert systems" for machine vision, may be integrated with the present system. Conveniently, the present system allows the setting of morphological requirements for test reporting. For example, a development of the FOBT color in the specific image region between the sample area and the developer front may be set as a requirement for a "positive" result within the test area.

Figure 2A:
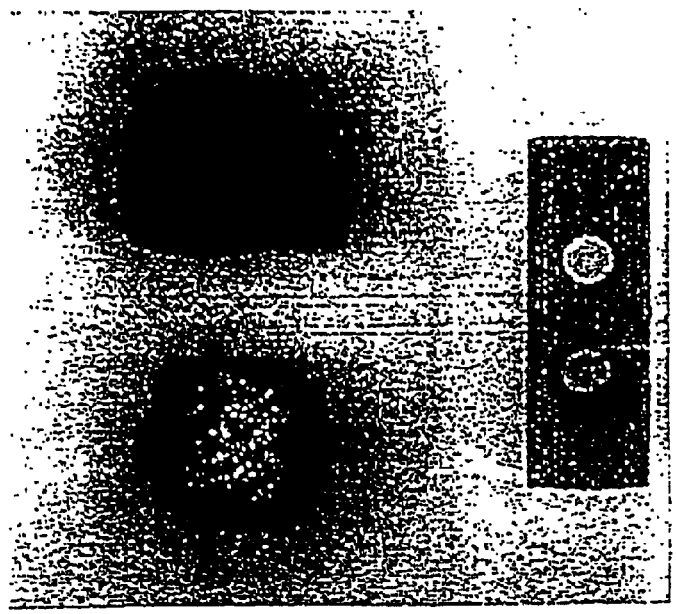
FIGS. 2A–2E illustrate hue angle image analysis according to one embodiment of the present invention.

In one embodiment of the present invention, a hue angle image analysis is used. FIGS. 2A–2E illustrate this method. FIG. 2A shows a raw image of the test area 2 in a form of an 8-bit Red/Green/Blue (RGB) image. The image is represented by an array of pixels. Each pixel contains color information broken down into red, green, or blue.

Figure 2B:
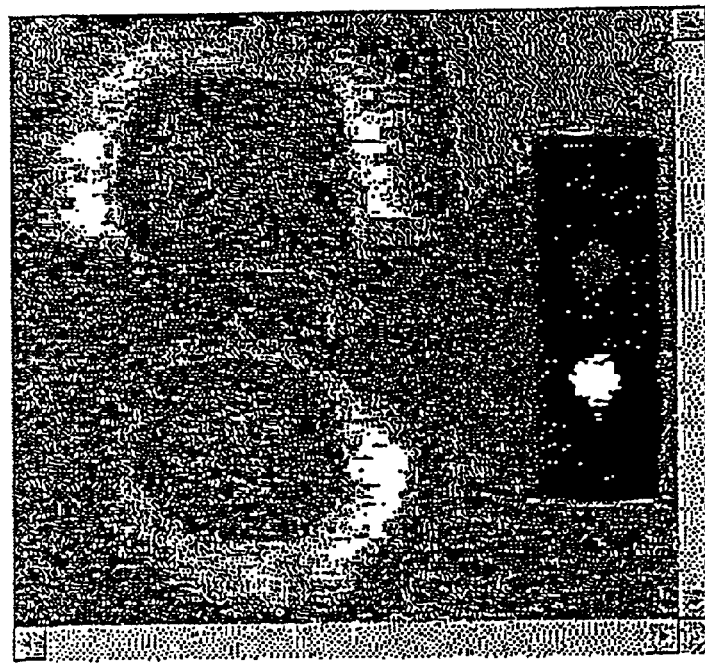
Figure 2C:

FIG. 2B shows a black-and-white 8-bit gray scale image obtained by applying a hue angle analysis algorithm to the raw image. FIG. 2C shows a digital "binary" image obtained from the 8-bit gray scale image shown in FIG. 2B. Black color (value "0") is assigned to the areas of the image with computed hue angles below a preset threshold value typical of positive FOBTs. White color (value "1") is assigned to tentative positive test patches of the image with computed hue angles above the threshold value.

Figure 2D:
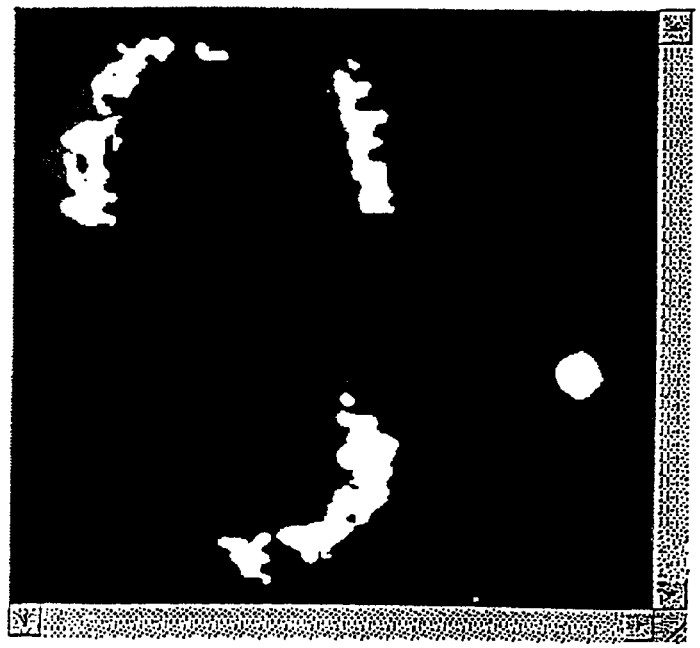
Figure 2E:
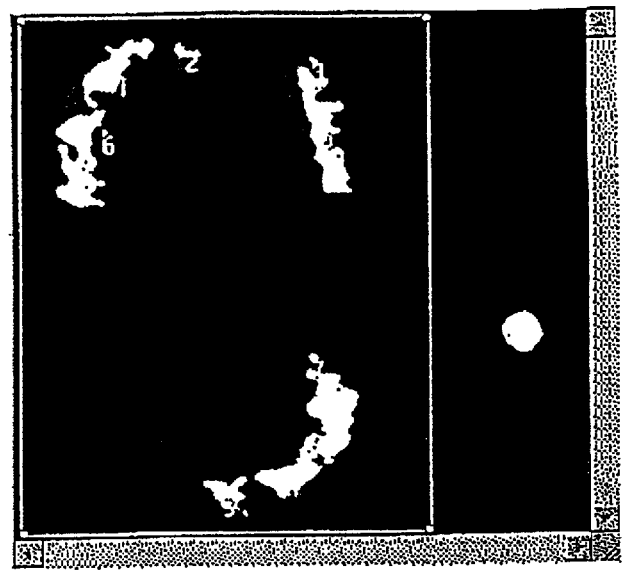

Referring to FIG. 2D, a median filter may be applied to the binary image shown in FIG. 2C to remove the "speckle" artifacts and to smooth the borders of the white objects. Finally, as shown in FIG. 2E, objects having dimensions below preset minimum values are rejected. The remaining objects are counted as positive test patches and their cumulative area is calculated and output to the file. Other parameters, such as mean radius, x/y location, roundness, etc., may be readily computed at this point.

In this simple processing method, a cumulative size of the identified positive patches is proportional to the amount of color developed on the test area, which reflects the amount of blood present in the fecal sample. Consequently, the calculated cumulative area of positive test patches may be used to estimate a relative mass of the blood present in the sample.

The instant system may generate a second digital image of the testing area of the FOBT device with graphical identification of the positive test patch(es) and other data processing results. The data processor may be easily adapted to store the raw and processed images and to generate a diagnostic report of the sample. A review of these electronic images could be conducted on-site, or at a remote central location using a conventional networked computer display to present the selected images for review. Off-line review permits greater convenience because the electronic images are indefinitely stable, whereas the color developed on the test device fades rapidly.

A digital format of the image also allows the display and/or storage of the image annotations (e.g., outlining of image features identified as FOBT positive) or the annotation of image data to document the time, date, location, method and results of image analysis. Image enhancement and image annotation, provided by the present invention, presents FOBT results in a format which is more meaningful to clinicians than the conventional ones.

Time permitting, multiple images for each test device may be acquired, perhaps including an image prior to the addition of the developer, and one or more subsequent images acquired at fixed or variable time intervals following the addition of the developer. The analysis of the data may then begin by subtracting the pre-developer image from subsequent images to better isolate FOBT development. Time-zero images may also be used to correct for uneven illumination. The image series may also be used in sophisticated analysis regimes which monitor the diffusion of the FOBT signal, or the rate of color change, permitting optimum sensitivity. Hardware and software for handling multiple images are well known in the art and will not be described here.

By utilizing an appropriate software, the system of the present invention may be configured to provide additional convenient features. For example, the system may provide the verification of the correct placement and a suitable quantity of stool sample and developer to the test area of the FOBT device. Automatic image registration may be also provided by utilizing special markers on the test devices. The present invention may also utilize positive and negative control indicators of the FOBT devices to verify a proper operation of the system. Those skilled in the art will recognize that algorithms for such optional system functions are known and can be easily adapted for use with the system of the present invention.

To minimize the size and/or cost of the system, a "satellite" instrument incorporating only an imaging sensor system, without any on-board image analysis capability, may be used. Such a simplified device may then transmit the test image results, together with identifying information, to a central computer for image analysis. The transmission of data could be done by conventional computer networks, including the Internet.

It is to be understood that the form of the device depicted in FIG. 1 has been chosen only for the purpose of describing a particular embodiment and function of the invention, and that the material of the invention can be addressed in various ways and incorporated in other types of devices.

Another aspect of the present invention provides a method of performing an FOBT on a fecal sample. The method comprises the steps of:

(a) placing the sample on a test area of the FOBT device;

(b) applying a developer to the test area to produce color patches on or around the sample;

(c) capturing an image of the test area with an image sensor and converting the image into digital data;

(d) comparing the digital data with predetermined threshold conditions of a positive FOBT by utilizing a data processor with a spectrographic and morphologic image analysis capability to identify at least one positive test patch; and (e) correlating a presence of a positive test patch on the test device with a presence of the occult blood in the sample.

Although this method can be used to analyze liquid, semi-solid, or solid samples applied to test devices, it is particular beneficial for use with solid and semi-solid fecal samples applied to a continuous test area of guaiac-based FOBT devices. For example, the present invention may be used in conjunction with HEMOCCULT® and HEMOCCULT® SENSA® FOBT devices (Beckman Coulter, Inc., CA).

In FOBTs, when the sample is spread on the test area, there is no optical signal produced above background noise level. An addition of a developer initiates a formation of color patches on or around the sample. By capturing an image of the entire testing area of the testing device, all developed color patches are evaluated against predetermined threshold conditions for a positive FOBT. Such an approach allows to achieve a higher accuracy of the test result and better sensitivity of the test as compared to a conventional method. In conventional methods, optical signals are measured in discrete areas of a test device (see, for example, the '535 patent). Since in FOBTs the color may develop essentially anywhere on the test area, the conventional approach would likely miss the developed color outside of the chosen discrete area and would obtain a false negative test result. In addition, the present invention focuses on the color and morphologic image of a sample by utilizing spectrographic and morphologic image analysis algorithm. This is different from the conventional method of the '535 patent in that the size and shape of the color image, no matter how irregular or discontinuous, can be read and interpreted. The colored object (or objects) seen by the '535 technique is always of defined size, shape, and area. The present invention looks for a colored object which does not have a defined size, shape, or area. The color may develop anywhere on the device and may be a spot, streak, blob, ring, etc.

The instant method may further comprise a step of determining a relative mass of the blood present in the sample by correlating the mass with a size of the positive test patch. If a plurality of positive test patches is identified, the relative mass of the blood present in the sample may be determined by correlating the mass with a cumulative size of the identified positive test patches.

In one embodiment, the method further comprises the steps of:

(a) generating a second image, wherein the image graphically identifies the positive test patch and other spectral data processing results; and (b) generating an analysis report in electronic form, the analysis report indicating test results, patient and test information.

The foregoing is meant to illustrate, but not to limit, the scope of the invention. Indeed, those of ordinary skill in the art can readily envision and produce further embodiments, based on the teachings herein, without undue experimentation.

EXAMPLE I

A series of HEMOCCULT® SENSA® slides containing stool samples spiked with different concentrations of whole blood was developed using HEMOCCULT® SENSA® developer. Thirty seconds after the addition of the developer, photographs of the HEMOCCULT® SENSA® slides were taken with a MAVICA® digital camera (Sony, Japan). The primary illumination was a single tungsten-halogen slide projector bulb. The obtained digital images were evaluated by utilizing a hue angle analysis outlined above and the object areas were calculated for each slide. The results are shown in Table 1, below.

Results

Figure 3:
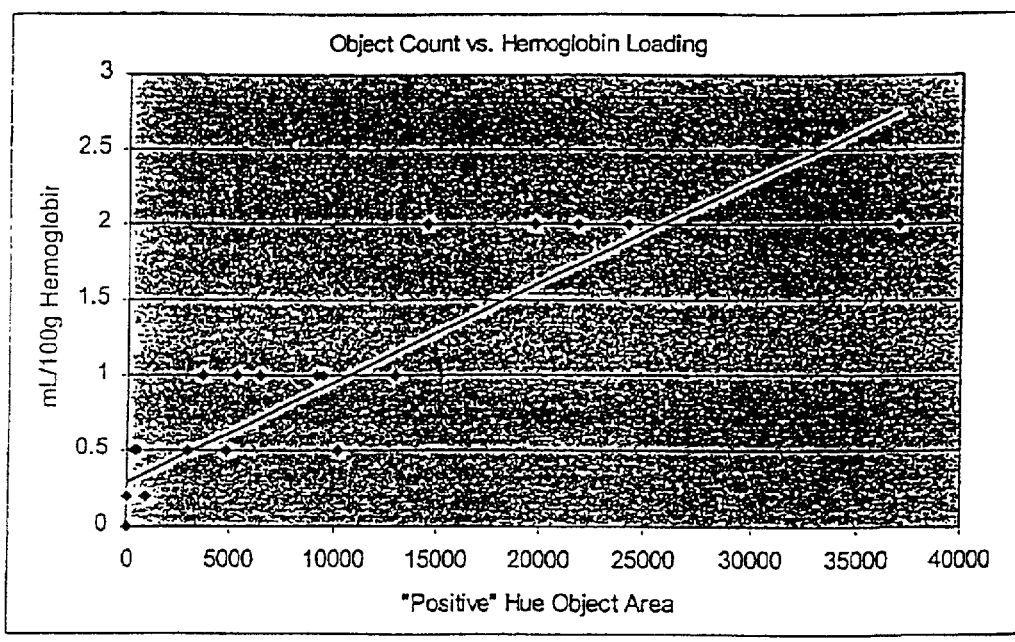
FIG. 3 is a graph showing a linear correlation between the size of the positive test patch and the concentration of hemoglobin in a sample.

When the object threshold was set at 200 units, all positive tests containing at least 0.5 mL blood/100 g stool and all negative tests were correctly identified. Referring to FIG. 3, the positive object area appeared to be semiquantitative for the blood levels in the sample test image data.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

TABLE 1

| Image | Test Result | Object Count | Object Area | Sample ID | Blood (mL) per 100 g of stool |
| --- | --- | --- | --- | --- | --- |
| Js44802.tif | NEGATIVE | 0 | 0 | A1 | 0.2 |
| Js44804.tif | POSITIVE | 1 | 855 | A1 | 0.2 |
| Js44805.tif | NEGATIVE | 0 | 0 | A9 | 0 |
| Js44806.tif | NEGATIVE | 0 | 0 | A9 | 0 |
| Js44807.tif | POSITIVE | 6 | 21742 | A2 | 2 |
| Js44808.tif | POSITIVE | 2 | 24138 | A2 | 2 |
| Js44809.tif | POSITIVE | 6 | 10202 | A6 | 0.5 |
| Js44810.tif | POSITIVE | 2 | 445 | A6 | 0.5 |
| Js44811.tif | POSITIVE | 6 | 12941 | A3 | 1 |
| Js44812.tif | POSITIVE | 3 | 5289 | A3 | 1 |
| Js44813.tif | POSITIVE | 7 | 9177 | A3 | 1 |
| Js44814.tif | POSITIVE | 4 | 4794 | A8 | 0.5 |
| Js44815.tif | POSITIVE | 2 | 2947 | A8 | 0.5 |
| Js44816.tif | POSITIVE | 1 | 339 | A8 | 0.5 |
| Js44817.tif | POSITIVE | 4 | 3586 | A7 | 1 |
| Js44818.tif | POSITIVE | 5 | 9391 | A7 | 1 |
| Js44819.tif | POSITIVE | 8 | 6443 | A7 | 1 |
| Js44820.tif | POSITIVE | 6 | 36955 | A5 | 2 |
| Js44821.tif | POSITIVE | 6 | 14445 | A5 | 2 |
| Js44822.tif | POSITIVE | 7 | 19677 | A5 | 2 |
| Js44823.tif | NEGATIVE | 0 | 0 | A4 | 0 |
| Js44824.tif | NEGATIVE | 0 | 0 | A4 | 0 |
| Js44825.tif | NEGATIVE | 0 | 0 | A4 | 0 |
| Js48803.tif | NEGATIVE | 0 | 0 | A1 | 0.2 |

What is claimed is:

1. A medical analysis system for reading and interpreting a fecal occult blood test (FOBT) device, the device having a continuous test area for spreading a fecal sample and adding a developer, wherein the developer is added to the test area containing the sample, the test area reacting with the sample and the developer producing color patches on or around the sample, the system comprising:

an image sensor for capturing an image of the entire test area of the FOBT device and for converting the image into a digital data, wherein the image of the entire test area of the FOBT device is captured by the image sensor; and a data processor conventionally coupled to the image sensor, wherein the data processor compares the digital data with predetermined threshold conditions of a positive FOBT by utilizing a spectrographic and morphologic image analysis algorithm and determines a presence of the occult blood in the sample, wherein the image sensor is selected from a group consisting of: charge-coupled devices (CCD), charge injection devices, translational stage and optical scanners, color complementary metallic oxide semiconductors, photovoltaic diode arrays, color video cameras with frame-grabbing software, and photographic film.

2. The system of claim 1, wherein the image sensor further comprises electronic and optical components necessary for capturing the image and converting it into the digital data.

3. The system of claim 1, wherein the optical components are selected from a group consisting of: lenses, mechanical or optical scanners, shutters, irises, and filters.

4. The system of claim 1, wherein the image sensor is a digital color camera.

5. The system of claim 1, wherein the image sensor is a digital monochrome camera having a plurality of color filters.

6. The system of claim 1, further comprising an illumination source for illumination of the test area of the FOBT device with a light.

7. The system of claim 1, further comprising a test device positioner for positioning and holding the FOBT device in a predetermined location.

8. The system of claim 1, further comprising an optical element position between the image sensor and the FOBT device to optimize a sensitivity of the image sensor to a desired color development and to minimize a scattered light background.

9. The system of claim 8, wherein said optical element is a polarizer or an optical filter.

10. A medical analysis system for reading and interpreting a fecal occult blood test (FOBT) device, the device having a continuous test area for spreading a fecal sample and adding a developer, wherein the developer is added to the test area containing the sample, the test area reacting with the sample and the developer producing color patches on or around the sample, the system comprising:

an image sensor for capturing an image of the entire test are of the FOBT device and for converting the image into a digital data, wherein the image of the entire test area of the FOBT device is captured by the image sensor; and a data processor conventionally coupled to the image sensor; and a data processor conventionally coupled to the image sensor, wherein the data processor compares the digital data with predetermined threshold conditions of a positive FOBT by utilizing a spectrographic and morphologic image analysis algorithm and determines a presence of the occult blood in the sample, wherein the data processor comprises a computer system and the image analysis algorithm is selected from a group consisting of: hue angle image analysis; a flat-fielding analysis for reducing a non-uniform illumination effect on the test sample; a vector analysis for better object discrimination in the image; an image factor analysis coupled with a principal component regression method for providing a multi-wavelength spectroscopic analysis of the image; a mean-centering analysis for reducing any illumination variance on the test sample during formation of the image; a morphological analysis; a feature-specific convolution analysis; and combinations thereof.

11. The system of claim 10, wherein the computer system utilizes the hue angle image analysis.

12. The system of claim 11, wherein the computer system determines a presence of the occult blood in the sample by identifying at least on positive test patch, wherein the positive test patch is identified by comparing the area of the color patch with a preselected threshold value.

13. The system of claim 12, wherein the computer system determines a relative mass of the blood present in the sample by correlating the mass with the area of the identified positive test patch.

14. The system of claim 13, wherein the computer identifies a plurality of positive test patches and determines the relative mass of the blood present in the sample by correlating the mass with a cumulative size or area of the identified positive test patches.

15. The system of claim 12, wherein the computer system generating a second image of the test area, wherein the image graphically identifies the positive test patch and other data processing results.

16. The system of claim 15, wherein the computer system stores the images, generates a diagnostic report of the sample, and electronically transmits the images or the diagnostic report to a user-specified destination through a computer network.

17. A medical analysis system for reading and interpreting a fecal occult blood test (FOBT) device, the device having a continuous test area for spreading a fecal sample and adding a developer, wherein the developer is added to the test area containing the sample, the test area reacting with the sample and the developer producing color patches on or around the sample, the system comprising:

an image sensor for capturing an image of the entire test area of the FOBT device and for converting the image into a digital data, wherein the image of the entire test area of the FOBT device is captured by the image sensor; and a data processor conventionally coupled to the image sensor, and a data processor conventionally coupled to the image sensor, wherein the data processor compares the digital data with predetermined threshold conditions of a positive FOBT by utilizing a spectrographic and morphologic image analysis algorithm and determines a presence of the occult blood in the sample, further comprising an illumination source for illumination of the test area of the FOBT device with a light, wherein the illumination source is selected from a group consisting of: incandescent lamps, fluorescent lamps, electrochemiluminescent devices, arc discharge lamps, stroboscopic-type flash lamps, light-emitting diodes, fiberoptic illuminators, lasers, and combinations thereof.

18. A medical analysis system for reading and interpreting a fecal occult blood test (FOBT) device, the device having a continuous test area for spreading a fecal sample and adding a developer, wherein the developer is added to the test area containing the sample, the test area reacting with the sample and the developer producing color patches on or around the sample, the system comprising:

an image sensor for capturing an image of the entire test area of the FOBT device and for converting the image into a digital data, wherein the image of the entire test area of the FOBT device is captured by the image sensor; and a data processor conventionally coupled to the image sensor, and a data processor conventionally coupled to the image sensor, wherein the data processor compares the digital data with predetermined threshold conditions of a positive FOBT by utilizing a spectrographic and morphologic image analysis algorithm and determines a presence of the occult blood in the sample, further comprising an illumination source for illumination of the test area of the FOBT device with a light, further comprising optical or electronic components for directing the light from the illuminating source onto the test area of the FOBT device, wherein the optical components are selected from a group consisting of: lenses, prisms, mechanical or optical scanners, shutters, irises, filters, fiber optical devices, and combinations thereof.

19. A medical analysis system for reading an interpreting a fecal occult blood test (FOBT) device, the device having a test area for placing a sample and adding a developer, wherein the developer is added to the test area containing the sample, the test area reacting with the sample and the developer producing one or more color patches on or around the sample, the system comprising:

an illumination source for illuminating the test area of the FOBT device with light;

an image sensor detecting the light reflected from the test area; the image sensor generating an image of the test area and converting the image into digital data, wherein the image of the entire test area of the FOBT device is captured by the image sensor, wherein the image sensor is selected from a group consisting of: charge-coupled devices (CCD), charge injection devices, translational stage and optical scanners, color complementary metallic oxide semiconductors, photovoltaic diode arrays, color video cameras with frame-grabbing software, and photographic film; and a data processor coupled to the image sensor, the data processor applying a hue angle analysis to the received digital data, comparing the digital data with predetermined threshold conditions of a positive FOBT, and identifying a positive test patch indicative of the presence of the occult blood in the sample.

20. The system of claim 19, wherein the data processor additionally determines a relative mass of the blood present in the sample by correlating the mass with the area of the positive test patch.

21. The system of claim 19, wherein the data processor comprises a computer system.

22. The system of claim 21, wherein the computer system generates a second image, wherein the image graphically identifies the positive test patch and other spectral data processing results.

23. The system of claim 22, wherein the computer system stores the images, generates a diagnostic report of the sample, and electronically transmits the images, and the diagnostic report to a user-specified destination through a computer network.

24. A method of performing a fecal occult blood test (FOBT) on a sample, the method comprising the steps of:

(a) placing the sample on a test area of the FOBT device;

(b) applying a developer to the test area to produce one or more color patches on or around the sample, wherein the developer is added to the test area containing the sample;

(c) capturing an image of the test area with an image sensor and converting the image into digital data, wherein the image of the entire test area of the FOBT device is captured by the image sensor;

(d) comparing the digital data with predetermined threshold conditions of a positive FOBT by utilizing a data processor with a spectrographic and morphologic image analysis capability to identify a positive test patch; and (e) correlating a presence of one or more positive test patches on the test device with a presence of the occult blood in the sample, wherein a type of the spectrographic and morphologic image analysis is selected from a group consisting of: hue angle image analysis, image factor analysis with principal components regression, mean-centering analysis, flat-fielding analysis, vector analysis, feature-specific convolution analysis, morphological analysis, and combinations thereof.

25. The method of claim 24, further comprising a step of:

determining a relative mass of the blood present in the sample by correlating the mass with the area of one or more positive test patches.

26. The method of claim 25 identifies a plurality of positive test patches and determines the relative mass of the blood present in the sample by correlating the mass with a cumulative size or area of the identified positive test patches.

27. The method of claim 24, further comprising steps of:

(a) generating a second image, wherein the image graphically identifies the positive test patch and other spectral data processing results; and (b) generating an analysis report in electronic form, the analysis report indicating test results, patient and test information.

* * * * *